United States Patent [19]

Mrowca

[11] 4,234,729
[45] Nov. 18, 1980

[54] PHOSPHINE OXIDE-SUBSTITUTED PYRIMIDINES

[75] Inventor: Joseph J. Mrowca, Wilmington, Del.

[73] Assignee: E. I. Du Pont de Nemours and Company, Wilmington, Del.

[21] Appl. No.: 49,481

[22] Filed: Jun. 18, 1979

[51] Int. Cl.³ .......................... C07F 9/65; C08K 5/53
[52] U.S. Cl. ............................ 544/243; 260/45.7 P; 544/232; 544/337
[58] Field of Search ........................................ 544/243

[56] References Cited

U.S. PATENT DOCUMENTS 3,316,293   4/1967   Carr et al. ........................... 544/243
3,852,362   12/1974   Lambert ........................ 260/606.5 P

OTHER PUBLICATIONS

Hewertson, et al., J. Chem. Soc., pp. 1020–1026 (1964).
Disteldorf, et al., Liebigs Ann. Chem., 1976, pp. 225–240 (1976).
Kosolapoff, et al., J. Org. Chem., 26, pp. 1895–1898 (1961).
Hewertson, et al., J. Chem. Soc., pp. 1670–1675 (1963).
Hewertson, et al., Chemical Abstracts, vol. 60, 14535f (1964).

Primary Examiner—Donald G. Daus
Assistant Examiner—Diana G. Rivers

[57] ABSTRACT

Phosphine oxide of the formula selected from the group consisting of

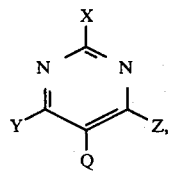

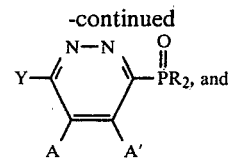

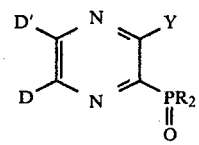

wherein
X is H, alkylthio of 1–4 carbon atoms, or

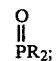

Y is H, alkyl of 1–4 carbon atoms, Cl, Br, or

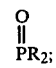

Z is H, alkyl of 1–4 carbon atoms, or

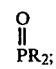

at least one of X, Y, and Z in the formula in which all three symbols appear is

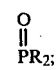

Q is H or Br;
each of A and A' is selected independently from H and alkyl of 1–4 carbon atoms, or A and A' taken jointly is CH=CH—CH=CH;
each of D and D' is selected independently from H and CN, or D and D' taken jointly is CH=CH—CH=CH; and
each R is selected independently from alkyl of 1–4 carbon atoms, cycloalkyl of 5–6 carbon atoms, benzyl, phenyl, tolyl, and chlorophenyl.

7 Claims, No Drawings

PHOSPHINE OXIDE-SUBSTITUTED PYRIMIDINES

DESCRIPTION

TECHNICAL FIELD

This invention relates to a phosphine oxide substituted pyridazine, pyrimidine or pyrazine which is useful as a flame retardant for polymeric materials.

BACKGROUND

Hewertson et al. in J. Chem. Soc., 1963, 1670 disclose the preparation of 2,4,6-tris(dialkoxyphosphinyl)-1,3,5-triazines from cyanuric chloride and trialkyl phosphites. Also disclosed is the tris(diphenylphosphinyl) derivative which decomposes above 300° C. and hydrolyzes readily to cyanuric acid and diphenylphosphinic acid. The preparation of bis(diphenylphosphinyl)-1,2,4,5-tetrazine is disclosed by Disteldorf et al. in Ann., 1976, 225. The preparation of various dialkyl 2-, 4- and 5-pyrimidylphosphonates is disclosed by Kosolapoff et al. in J. Org. Chem., 26, 1895 (1961).

DISCLOSURE OF INVENTION

For further comprehension of the invention and of the objects and advantages thereof reference may be made to the following description and to the appended claims in which the various novel features of the invention are more particularly set forth.

The invention resides in a phosphine oxide which is useful as a flame retardant for polymeric materials. More particularly, the invention resides in a phosphine oxide wherein each of the one or more phosphorus atoms is bonded to a carbon atom of a pyridazine, pyrimidine or pyrazine nucleus. The phosphine oxide is of the formula selected from the group consisting of

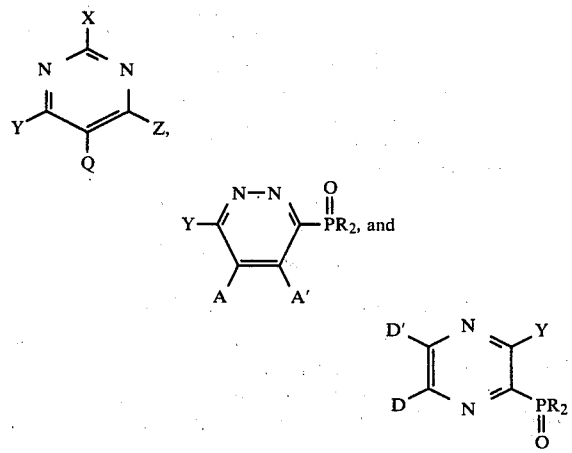

wherein

X is H, alkylthio of 1–4 carbon atoms, or

Y is H, alkyl of 1–4 carbon atoms, Cl, Br, or

Z is H, alkyl of 1–4 carbon atoms, or

at least one of X, Y, and Z in the formula in which all three symbols appear is

Q is H or Br;

each of A and A' is selected independently from H and alkyl of 1–4 carbon atoms, or A and A' taken jointly is CH=CH-CH=CH;

each of D and D' d is selected independently from H and CN, or D and D' taken jointly is CH=CH-CH=CH; and each R is selected independently from alkyl of 1–4 carbon atoms, cycloalkyl of 5–6 carbon atoms, benzyl, phenyl, tolyl, and chlorophenyl.

Examples of operable alkylthio groups in the definition of X include methylthio, propylthio, and isobutylthio. Examples of operable alkyl groups in the definitions of Y, Z, A, A' and R include methyl, ethyl, isopropyl, butyl, and t-butyl. Because of the availability of starting materials, both R groups are preferably the same.

It is anticipated that, in place of dichlorobenzene, other solvents would be operable. These include chlorobenzene, toluene, and acetonitrile, but longer reaction times would probably be required because of the lower boiling points of such solvents in an open system. It is also anticipated that the process would be operable in the absence of a solvent, but use of a solvent helps moderate the reaction and control the temperature.

Alternatively, the alkyl phosphinite can be formed in situ from the corresponding dihydrocarbylphosphinous chloride and the appropriate thallium alkoxide, and then reacted, without isolation, with the appropriate pyridazine, pyrimidine or pyrazine. This method is illustrated in Example 10.

The phosphine oxide product of the invention is a colorless or nearly colorless crystalline solid that is stable to moisture (hydrolysis). The preferred phosphine oxide has two or three phosphinyl groups, especially the latter, because of its higher phosphorus content, thus imparting a greater flame-retardancy characteristic to the phosphine oxide.

As shown in the following experiments the phosphine oxide product of the invention is useful as a flame retardant for polymeric materials, particularly polyesters and polyamides. At least a flame-retarding amount, determined for each combination of phosphine oxide and polymer by experimentation, is incorporated in the polymer, either on the surface or intimately dispersed throughout, preferably the latter. The procedure used to evaluate the flame retardancy of the phosphine oxide is described below.

Ten grams of a mixture of powdered polymer and the flame-retardant is thoroughly blended. The mixture is pressed into a film containing a Fiberglas ® scrim at 5000 lb (2270 kg) ram pressure in a press at an appropriate temperature, about 20°–30° C. above the melting point of the polymer, and then quenched in ice water. The films thus prepared are cut into 1.25×3-inch (3.18×7.62-cm) strips and each film is weighed. The film is then held in a U-clamp in a horizontal plane in a vented burn chamber. One exposed edge of the film is ignited for 5 seonds with a gas flame 0.75 inch (1.9 cm) high, and the time required for the flame front to travel from a line 0.5 inch (1.3 cm) from the ignited edge to a line 2.5 inches (6.4 cm) from the ignited edge, or until the flame goes out, is determined. A burn rate, in inches (cm) per minute, is calculated from a data.

From my experience it has been determined that the burn rate is inversely proportional to the mass of polymer being burned. Therefore, it is necessary to normalize the aforesaid data to a constant polymer weight. This is done by subtracting the scrim weight (constant) from the specimen weight to obtain the polymer weight and multiplying the aforesaid burn rate by the ratio of the reference polymer weight (no additive) to the test polymer weight (including additive). The normalized rates from a minimum of six specimens of each composition tested are averaged and compared with data from control samples of the pure polymer to establish the relative effectiveness of the additive on the burn rate.

The results obtained, using the phosphine oxides of Examples 1, 3, 4 and 6, are given in the following table. It may be noted that all the test compounds lowered the burn rates at low additive levels (2% and 4%), except for the last compound in 66 nylon.

TABLE

| Product of Ex. | Wt. % Additive | Polymer* | Burn rate, inches/min (cm/min) | |
|---|---|---|---|---|
| | | | No Additive | With Additive |
| 3 | 8 | 2GT | 3.00 (7.62) | 1.72 (4.37) |
| 4 | 5 | 2GT | 3.00 (7.62) | 2.14 (5.44) |
| 1 | 5 | 2GT | 3.00 (7.62) | 2.51 (6.38) |
| 6 | 2 | 2GT | 3.00 (7.62) | 2.41 (6.12) |
| 6 | 4 | 2GT | 3.00 (7.62) | 2.01 (5.11) |
| 6 | 5 | 2GT | 3.00 (7.62) | 1.88 (4.78) |
| 6 | 4 | 4GT | 3.30 (8.38) | 2.77 (7.04) |
| 6 | 2 | 66 | 1.65 (4.19) | 1.65 (4.19) |
| 6 | 4 | 66 | 1.65 (4.19) | 1.70** (4.32) |
| 6 | 5 | 66 | 1.65 (4.19) | 1.52 (3.86) |

*2GT is poly(ethylene terephthalate)
4GT is poly(tetramethylene terephthalate)
66 is poly(hexamethyleneadipamide)
**Flame went out in two of six runs The following examples illustrate the preparation of the phosphine oxide product of the invention. In these examples the products are named as disubstituted phosphinyl derivatives of pyridazine, pyrimidine, and pyrazine. They can also be named as trisubstituted phosphine oxides. Thus, in Example 1 the product 2,3-dicyano-5,6-bis(diphenylphosphinyl)-pyrazine can also be named 2,3-dicyano-5,6-pyrazinediylbis(diphenylphosphine oxide); in Example 2 the product 5-bromo-4-diphenylphosphinyl-2-methylthiopyrimidine can also be named 5-bromo-2-methylthio-4-pyrimidinyldiphenylphosphine oxide.

EXAMPLE 1

2,3-Dicyano-5,6-bis(diphenylphosphinyl)pyrazine

To a stirred, refluxing solution of 5.00 g of 2,3-dicyano-5,6-dichloropyrazine in 100 ml of o-dichlorobenzene under nitrogen was added dropwise 10.00 g of methyl diphenylphosphinite. After the addition was completed, the mixture was refluxed for 4 hours and then allowed to stand overnight. The resulting solid was separated by filtration, washed with benzene and twice with hexane, recrystallized from 200 ml of o-dichlorobenzene, and dried at 80° C./0.1 mm (13 Pa) to give 8.08 g of 2,3-dicyano-5,6-bis(diphenylphosphinyl)-pyrazine (shown by formula in Claim 5) as a white solid, decomposition beginning at 210° C. Anal. calcd for $C_{30}H_{20}N_4O_2P_2$: C, 67.93; H, 3.80; N, 10.56; P, 11.68. Found: C, 67.77; H, 3.92; N, 10.48; P, 11.18.

If ethyl diethylphosphinite is substituted for methyl diphenylphosphinite in substantially the same aforesaid procedure of this example, 2,3-dicyano-5,6-bis(diethylphosphinyl)pyrazine will be formed. If methyl di-o-tolylphosphinite is used, the product will be 2,3-dicyano-5,6-bis(di-o-tolylphosphinyl)-pyrazine.

EXAMPLE 2

5-Bromo-4-diphenylphosphinyl-2-methylthiopyrimidine

To a stirred, refluxing mixture of 3.56 g of 5-bromo-4-chloro-2-methylthiopyrimidine in 100 ml of o-dichlorobenzene under nitrogen was added dropwise 10.00 g of methyl diphenylphosphinite. After the addition was completed, the mixture was refluxed for 6 hours and then allowed to cool. Volatiles were removed from the mixture under vacuum, and the residue was recrystallized from 30 ml of 1-chlorobutane and dried at 50° C./0.1 mm (13 Pa) to give 2.97 g of 5-bromo-4-diphenylphosphinyl-2-methylthiopyrimidine (shown by formula in Claim 7) as white crystals, mp 124°–127° C. Anal. Calcd for $C_{17}H_{14}BrN_2OPS$: C, 50.39; H, 3.48; N, 6.91. Found: C, 50.54; H, 3.67; N, 6.84.

If 4-chloro-2-ethylthio-6-methylpyrimidine is used in place of 5-bromo-4-chloro-2-methylthiopyrimidine in substantially the same aforesaid procedure of this example, 4-diphenylphosphinyl-2-ethylthio-6-methylpyrimidine will be formed. If 2-chloropyrimidine is used, the product will be 2-diphenylphosphinylpyrimidine.

EXAMPLE 3

4,6-Bis-(diphenylphosphinyl)-2-methylthiopyrimidine

To a stirred refluxing solution of 5.00 g of 4,6-dichloro-2-methylthiopyrimidine in 150 ml of o-dichlorobenzene under nitrogen was added dropwise 15.00 g of methyl diphenylphosphinite over 35 minutes. The mixture was refluxed for 5.5 hours after the addition was completed and then allowed to cool, at which time it was added to 850 ml of n-hexane. The resulting solid was separated by filtration, washed with n-hexane, and recrystallized from 100 ml of ethanol to give 11.00 g of 4,6-bis(diphenylphosphinyl)-2-methylthiopyrimidine (shown by formula in Claim 8) as white crystals, mp 221°–222° C. Anal. Calcd for $C_{29}H_{24}N_2O_2P_2S$: C, 66.15; H, 4.59; N, 5.32. Found: C, 65.59; 65.59; H, 4.54, 4.75; N, 5.04, 5.01.

If methyl ethylmethylphosphinite is used in place of methyl diphenylphosphinite in substantially the same aforesaid procedure of this example, 4,6-bis-(ethylmethylphosphinyl)-2-methylthiopyrimidine will be formed. If ethyl dibutylphosphinite is used, the product will be 4,6-bis(dibutylphosphinyl)-2-methylthiopyrimidine. If ethyl bis(2-chlorophenyl)phosphinite is used, the product will be 4,6-bis[bis-(2-chlorophenylphosphinyl)]-2-methylthiopyrimidine.

EXAMPLE 4

2,3-Bis(diphenylphosphinyl)quinoxaline

To a stirred, refluxing mixture of 5.00 g of 2,3-dichloroquinoxaline in 100 ml of o-dichlorobenzene under nitrogen was added dropwise 14.00 g of methyl diphenylphosphinite. The mixture was refluxed for 6 hours after the addition was completed and then allowed to stand overnight at room temperature. The next day the mixture was admixed with 500 ml of n-hexane, and the resulting solid was separated by filtration, washed with hexane, recrystallized from 100 ml of chlorobenzene, and dried at 100° C./0.1 mm (13 Pa) to give 9.87 g of 2,3-bis(diphenylphosphinyl)-quinoxaline (shown by formula in Claim 6) as a very slightly yellowish-white solid, mp 258°–272° C. with decomposition. Anal. Calcd for $C_{32}H_{24}N_2O_2P_2$: C, 72.45; H, 4.56; N, 5.28; P, 11.68. Found: C, 72.38; H, 4.23; N, 5.18; P, 11.39.

If 2-chloroquinoxaline is used in place of 2,3-dichloroquinoxaline in substantially the same aforesaid procedure of this example, 2-diphenylphosphinylquinoxaline will be formed. If 2-chloro-3-methylquinoxaline is used, the product will be 2-diphenylphosphinyl-3-methylquinoxaline.

EXAMPLE 5

4,6-Bis(diphenylphosphinyl)pyrimidine

To a stirred, refluxing mixture of 5.00 g 4,6-dichloropyrimidine in 100 of o-dichlorobenzene under nitrogen was added dropwise 17.00 g of methyl diphenylphosphinite. After the addition was completed, the mixture was refluxed for 6.5 hours and then allowed to cool. The cooled mixture was added to 750 ml of n-hexane, and the white solid that formed was separated by filtration, washed with n-hexane, recrystallized from 150 ml of toluene, and dried at 100° C./0.1 mm (13 Pa) to give 13.64 g of 4,6-bis(diphenylphosphinyl)pyrimidine (shown by formula in Claim 9) as cream-colored crystals, mp 213°–215° C. Anal. Calcd for $C_{28}H_{22}N_2O_2P_2$: C, 70.00; H, 4.62; N, 5.83; P, 12.89. Found: C, 69.80; H, 4.65; N, 5.65; P, 12.89.

If 2,4-dichloropyrimidine is used in place of 4,6-dichloropyrimidine in substantially the same aforesaid procedure of this example, the product will be 2,4-bis(-diphenylphosphinyl)pyrimidine. If 2,4-dichloro-6-methylpyrimidine is used, the product will be 2,4-bis(diphenylphosphinyl)-6-methylpyrimidine.

EXAMPLE 6

2,4,6-Tris(diphenylphosphinyl)pyrimidine

To a stirred, refluxing mixture of 5.00 g of 2,4,6-trichloropyrimidine in 100 ml of o-dichlorobenzene under nitrogen was added dropwise 26.00 g of methyl diphenylphosphinite. After the addition was completed, the mixture was refluxed for 6.5 hours and then allowed to stand overnight at room temperature. The next day a small amount of the solvent was removed by boiling, and the solution was allowed to stand again overnight. The next day the resulting solid was separated by filtration, washed twice with benzene and three times with hexane, recrystallized from 650 ml of toluene, and dried at 100° C./0.1 mm (13 Pa) to give 11.35 g of 2,4,6-tris(diphenylphosphinyl)pyrimidine (shown by formula in Claim 10) as a white solid, mp 235°–236° C. Anal. Calcd for $C_{40}H_{31}N_2O_3P_3$: C, 70.59; H, 4.59; N, 4.12; P, 13.65. Found: C, 70.72; H, 4.90; N, 3.92; P, 13.61.

If methyl ethylphenylphosphinite is used in place of methyl diphenylphosphinite in substantially the same aforesaid procedure of this example, 2,4,6-tris(ethylphenylphosphinyl)pyrimidine will be formed. If ethyl dipropylphosphinite is used, the product will be 2,4,6-tris(dipropylphosphinyl)pyrimidine. If methyl diisobutylphosphinite is used, 2,4,6-tris(isobutylphosphinyl)-pyrimidine will be formed. If ethyl dibenzylphosphinite is used, the product will be 2,4,6-tris(dibenzylphosphinyl)pyrimidine.

EXAMPLE 7

1,4-Bis(diphenylphosphinyl)phthalazine

To a stirred, refluxing mixture of 5.00 g of 1,4-dichlorophthalazine in 50 ml of o-dichlorobenzene under nitrogen was added dropwise 15.00 of methyl diphenylphosphinite. After the addition was completed, the mixture was refluxed for 6 hours and then allowed to stand at room temperature for 13 days. The resulting solid was separated by filtration, washed with benzene and with hexane, recrystallized from 125 ml of toluene with decolorizing charcoal treatment, and dried at 100° C./0.1 mm (13 Pa) to give 6.41 g of 1,4-bis(diphenylphosphinyl)phthalazine (shown by formula in Claim 13) as a light-yellow solid, mp 225°–228.5° C. Anal. Calcd $C_{32}H_{24}N_2O_2P_2$: C, 72.45; H, 4.56; N, 5.28; P, 11.68. Found: C, 72.49; H, 4.62; N, 5.36; P, 11.95.

If ethyl bis(4-chlorophenyl)phosphinite is used in place of methyl diphenylphosphinite in substantially the same aforesaid procedure of this example, the product will be 1,4-bis[bis(4-chlorophenylphosphinyl)]phthalazine. If methyl ethyl-o-tolylphosphinite is used, the product will be 1,4-bis-(ethyl-o-tolylphosphinyl)phthalazine. If methyl diisopropylphosphinite is used, the product will be 1,4-bis(diisopropylphosphinyl)phthalazine.

EXAMPLE 8

4,6-Bis(dicyclohexylphosphinyl)-2-methylthiopyrimidine

A mixture of 2.50 g of methyl dicyclohexylphosphinite and 1.00 g of 4,6-dichloro-2-methylthiopyrimidine in 20 ml of o-dichlorobenzene was refluxed under nitrogen for 6.5 hours. Volatiles were removed from the mixture under vacuum, and the resulting oily residue was recrystallized twice from cyclohexane with decolorizing charcoal treatment and dried at 100° C./0.1 mm (13 Pa) to give 0.15 g of 4,6-bis(dicyclohexylphosphinyl)-2-methylthiopyrimidine (shown by formula in Claim 11) as white crystals, mp 197°–198.5° C. Anal. Calcd for $C_{29}H_{48}N_2O_2P_2S$: C, 63.25; H, 8.79; N, 5.07; S, 5.82. Found: C, 63.19; H, 8.81; N, 4.89; S, 6.04.

If methyl dicyclopentylphosphinite is used in place of methyl dicyclohexylphosphinite in substantially the same aforesaid procedure, the product will be 4,6-bis(-dicyclopentylphosphinyl)-2-methylthiopyrimidine.

EXAMPLE 9

3,6Bis(diphenylphosphinyl)pyridazine

To a stirred, refluxing solutionof 3.00 g of 3,6-dichloropyridazine in 50 ml of o-dichlorobenzene under nitrogen was added dropwise 10.00 g of methyl diphenylphosphinite. After the addition was completed, the mixture was refluxed for 7 hours and then cooled. The cooled mixture was mixed with excess hexane; the oil which formed slowly crystallized. The resultant solid was separated by filtration, washed with hexane, and recrystallized twice from ethanol with decolorizing charcoal treatment to give 0.93 g of 3,6-bis-(diphenylphosphinyl)pyridazine (shown by formula in Claim 14) as slightly off-white crystals, mp 248°–251.5° C. Anal. Calcd for $C_{28}H_{22}N_2O_2P_2$: C, 70.00; H, 4.62; N, 5.83; P, 12.89. Found: C, 69.72; H, 4.92; N, 5.78; P, 12.82.

If 3-chloro-6-ethylpyridazine is used in place of 3,6-dichloropyradizine in substantially the same aforesaid procedure of this example, the product will be 3-diphenylphosphinyl-6-ethylpyridazine. If 3,6-dichloro-4-methylpyridazine is used, the product will be 3,6-bis(-diphenylphosphinyl)-4-methylpyridazine. If 3,6-dichloro-4,5-dimethylpyridazine is used, 3,6-bis(diphenylphosphinyl)-4,5-dimethylpyridazine will be the product.

EXAMPLE 10

4-Chloro-6-dimethylphosphinyl-2-methylthiopyrimidine

To a stirred solution of 3.84 g of dimethylphosphinous chloride in 50 ml of degassed dry toluene under nitrogen was added 10.00 g of thallous ethoxide. The mixture was stirred for 2 hours and filtered, and to the filtrate was added 3.25 g of 4,6-dichloro-2-methylthiopyrimidine. The mixture was heated to boiling and cooled to room temperature five times and then stirred overnight. The mixture was filtered, and the filtrate was evaporated under vacuum. The residue partially crystallized on standing. The solid was separated and recrystallized from 10 ml of toluene to give 0.40 of 4-chloro-6-dimethylphosphinyl-2-methylthiopyrimidine (shown by formula in Claim 12) as a light-yellow solid, mp 172°–182° C. with decomposition. Anal. Calcd for $C_7H_{10}ClN\, OPS$: C, 35.53; H, 4.26; N, 11.84. Found: C, 35.30, 35.17; H, 4.53, 4.44; N, 11.44, 11.58.

If 4,6-dibromo-2-methylthiopyrimidine is used instead of the 4,6-dichloro compound in substantially the same aforesaid procedure of this example, 4-bromo-6-dimethylphosphinyl-2-methylthiopyrimidine will be formed.

BEST MODE FOR CARRYING OUT THE INVENTION

The most preferred phosphine oxide, that is, one having three phosphinyl groups, can be prepared by hereinabove as being the best method based on experience.

INDUSTRIAL APPLICABILITY

This phosphine oxide of the invention is useful as a flame retardant for polymeric materials, particularly polyesters and polyamides. Such materials are commonly employed in the textile industry.

I claim:
1. Phosphine oxide of the formula

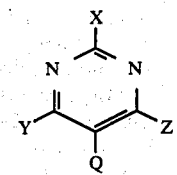

wherein
X is H, alkylthio of 1–4 carbon atoms, or

Y is H, alkyl of 1–4 carbon atoms, Cl, Br, or

Z is H, alkyl of 1–4 carbon atoms, or

at least one of X, Y, and Z is

Q is H or Br; and
each R is selected independently from alkyl of 1–4 carbon atoms, cycloalkyl of 5–6 carbon atoms, benzyl, phenyl, tolyl, and chlorophenyl.

2. Phosphine oxide of claim 1 of the formula

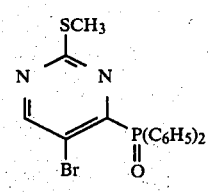

3. Phosphine oxide of claim 1 of the formula

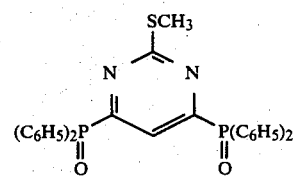

4. Phosphine oxide of claim 1 of the formula

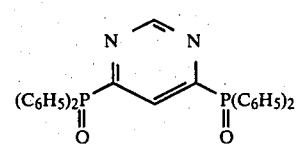

5. Phosphine oxide of claim 1 of the formula

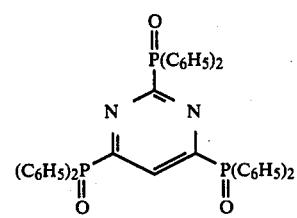
6. Phosphine oxide of claim 1 of the formula
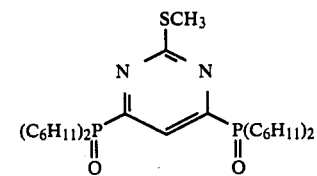
7. Phosphine oxide of claim 1 of the formula
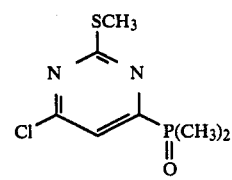
* * * * *

UNITED STATES PATENT AND TRADEMARK OFFICE
CERTIFICATE OF CORRECTION

PATENT NO. : 4,234,729

DATED : Nov. 18, 1980

INVENTOR(S) : Joseph J. Mrowca

It is certified that error appears in the above—identified patent and that said Letters Patent is hereby corrected as shown below:

Column 2, line 36, insert following paragraph:

-- Generally, based on my experience, the best method of preparing the phosphine oxide of the invention, as is illustrated in the examples which follow, is to heat, at reflux temperature, a solution in o-dichlorobenzene of:
(1) the methyl or ethyl ester of the appropriate disubstituted phosphinous acid (that is, the alkyl phosphinite); and (2) the appropriate pyridazine, pyrimidine, or pyrazine containing one or more chloro substituents in the position or positions into which it is desired to introduce one or more disubstituted phosphinyl groups.  Higher alkyl phosphinites can be used, but the methyl and ethyl esters are preferred because the by-product methyl chloride and ethyl chloride, respectively, are low-boiling and, therefore, can be easily removed from the reaction mixture.  Bromo or iodo substituents can be used in place of the chloro substituent, but these are less preferred because the bromo and iodo substituted materials are less readily available and the resultant by-products are less volatile.  The progress of the reaction can be followed by noting the evolution of alkyl halide formed as a by-product.  --

Column 4, line 17, delete "(shown by formula in Claim 5)".

Column 4, line 42, "Claim 7" should read -- Claim 2 --.

Column 4, line 65, "Claim 8" should read -- Claim 3 --.

Column 5, line 24, delete "(shown by formula in Claim 6)".

UNITED STATES PATENT AND TRADEMARK OFFICE
CERTIFICATE OF CORRECTION

PATENT NO. : 4,234,729

DATED : Nov. 18, 1980

INVENTOR(S) : Joseph J. Mrowca

It is certified that error appears in the above—identified patent and that said Letters Patent is hereby corrected as shown below:

Column 5, line 49, "Claim 9" should read -- Claim 4 --.

Column 6, line 7, "Claim 10" should read -- Claim 5 --.

Column 6, line 35, delete "(shown by formula in Claim 13)".

Column 6, line 62, "Claim 11" should read -- Claim 6 --.

Column 7, line 15, delete "(shown by formula in Claim 14)".

Column 7, line 45, "Claim 12" should read -- Claim 7 --.

Signed and Sealed this

Twenty-third Day of February 1982

[SEAL]

*Attest:*

*Attesting Officer*

GERALD J. MOSSINGHOFF

*Commissioner of Patents and Trademarks*